(12) United States Patent
Kamins

(10) Patent No.: US 7,235,475 B2
(45) Date of Patent: Jun. 26, 2007

(54) SEMICONDUCTOR NANOWIRE FLUID SENSOR AND METHOD FOR FABRICATING THE SAME

(75) Inventor: Theodore I. Kamins, Palo Alto, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 187 days.

(21) Appl. No.: 11/022,123

(22) Filed: Dec. 23, 2004

(65) Prior Publication Data

US 2006/0138575 A1 Jun. 29, 2006

(51) Int. Cl.
*H01L 21/4763* (2006.01)

(52) U.S. Cl. .................. 438/618; 438/666; 257/22; 977/700; 977/720; 977/731

(58) Field of Classification Search ................ 438/618, 438/666; 257/E21.305, E21.705, 930, 777, 257/22; 977/700–963
See application file for complete search history.

(56) References Cited

U.S. PATENT DOCUMENTS

| 2004/0079278 A1 | 4/2004 | Kamins et al. |
| 2004/0082178 A1 | 4/2004 | Kamins et al. |
| 2005/0133476 A1* | 6/2005 | Islam et al. ............... 216/2 |
| 2005/0212531 A1* | 9/2005 | Wei ........................ 324/664 |

* cited by examiner

*Primary Examiner*—Hsien-Ming Lee

(57) ABSTRACT

Nanowire fluid sensors are provided. The fluid sensors comprise a first electrode, a second electrode, and at least one nanowire between the first electrode and the second electrode. Each nanowire is connected at a first end to the first electrode and at a second end to the second electrode. Methods of fabricating and operating the fluid sensor are also provided.

16 Claims, 3 Drawing Sheets

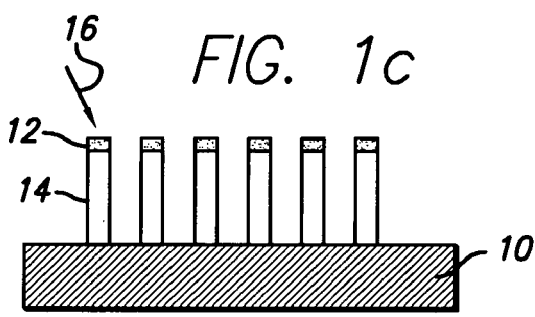
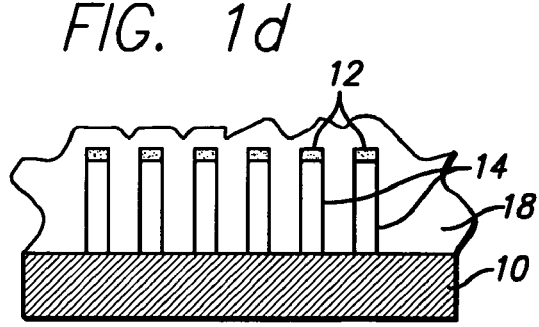
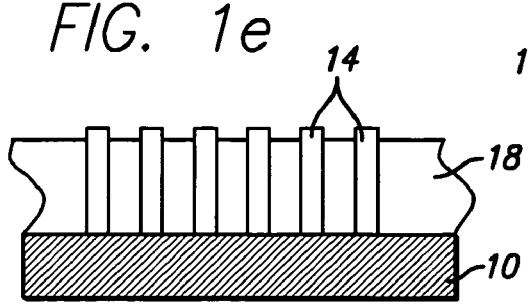
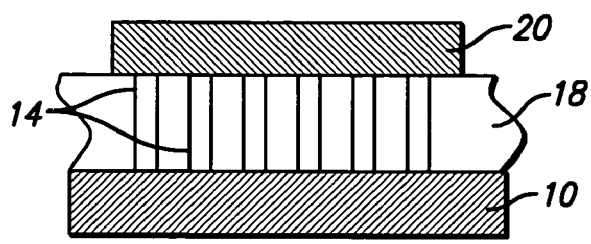
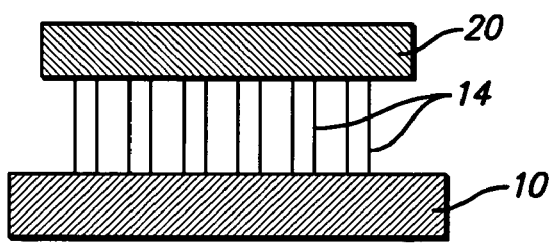
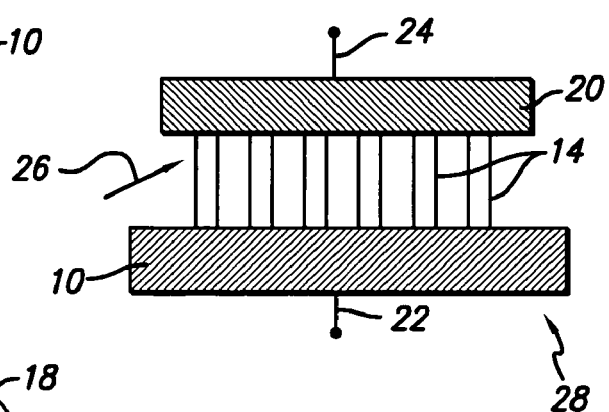

FIG. 3a
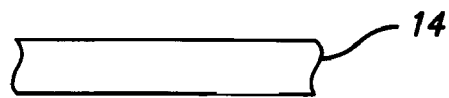
FIG. 3b
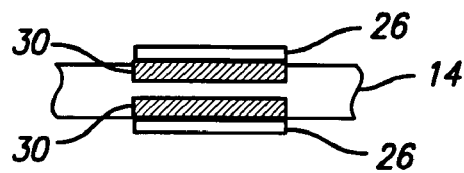
FIG. 3c
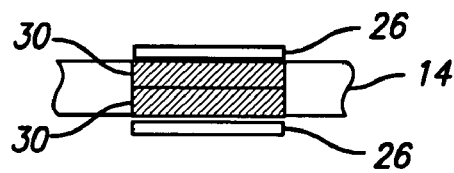
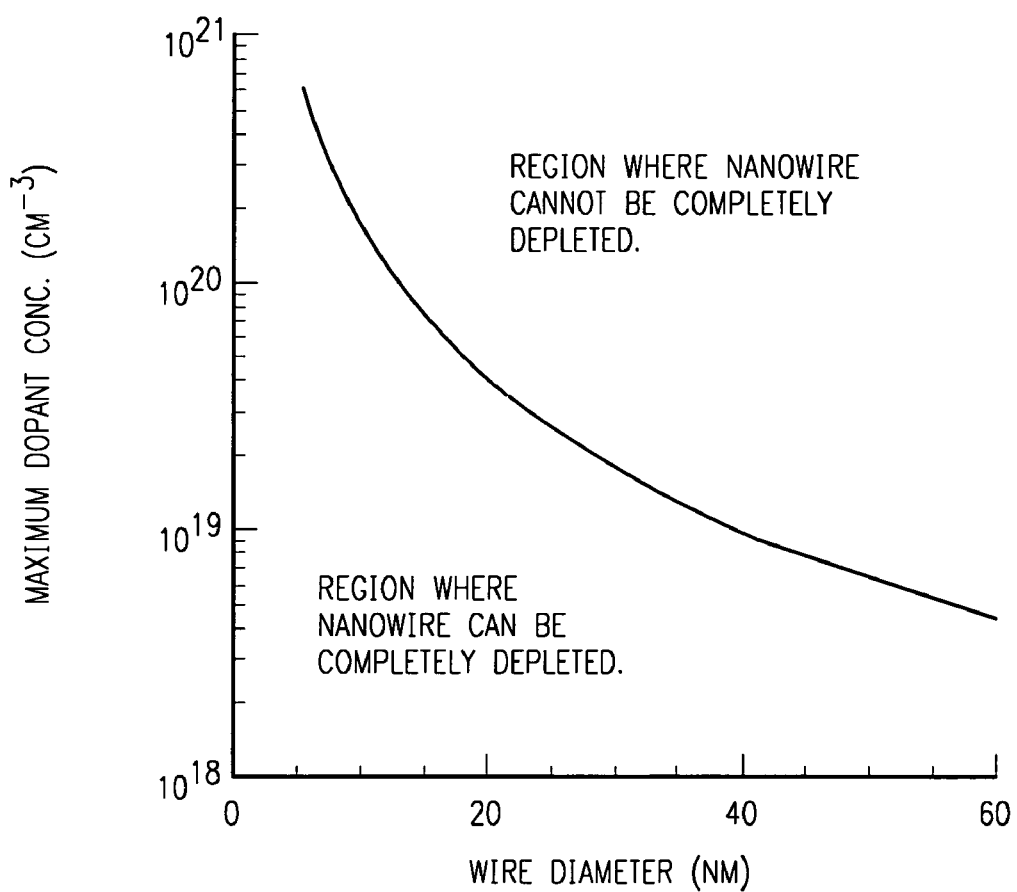
FIG. 4

SEMICONDUCTOR NANOWIRE FLUID SENSOR AND METHOD FOR FABRICATING THE SAME

TECHNICAL FIELD

The present invention is to fluid sensors, and, more particularly, to fluid sensors employing semiconductor nanowires.

BACKGROUND ART

Sensors detecting species in fluids (gas or liquids) have become increasingly important in recent years. Solid-state fluid sensors are particular valuable because of their small size and mechanical robustness.

The ability to detect a small quantity of a species in a fluid with a solid-state sensor relies on having a large surface area where the fluid can interact with the sensor. Detection often relies on sensing a property such as a change in resistance, so the volume of the sensing element should be reduced as much as feasible to increase the surface to volume ratio; e.g., the fraction of the volume that is affected by surface changes.

Forming a large number of small sensing elements that can act in parallel is thus advantageous for providing a large signal, but using lithography to define the elements can be expensive. A technique that does not use fine-scale lithography or patterning techniques is advantageous. Making contact without detailed patterning is also important.

DISCLOSURE OF INVENTION

In accordance with the embodiments disclosed herein, semiconductor nanowire fluid sensors and methods for fabricating and using the fluid sensors are provided.

The fluid sensor comprises a first electrode, a second electrode, and at least one nanowire between the first electrode and the second electrode. Each nanowire is connected at a first end to the first electrode and at a second end to the second electrode.

A method for making a fluid sensor is provided. The method comprises: providing a substrate including a first electrode, forming at least one metal nanoparticle on the substrate, exposing the metal nanoparticle(s) to at least one gas containing a semiconductor for a period of time sufficient to grow a corresponding at least one nanowire of a first predetermined length, forming a layer of an etchable material on the substrate and surrounding each nanowire; thinning the layer of the etchable material, if necessary, to expose top(s) of the nanowire(s) and simultaneously removing the upper portion(s) of the nanowire(s), if necessary, thereby providing the nanowire(s) with a second predetermined length that is less than the first predetermined length, depositing a layer of a metal on top of the layer of etchable material and patterning the layer of etchable material to form a second electrode; and at least partially removing the layer of the etchable material, sufficient to expose at least one of the nanowires.

A method for operating a fluid sensor is provided. The method comprises: providing a fluid sensor, introducing at least one fluid to the fluid sensor; and determining an aspect of the fluid(s). The fluid sensor comprises a first electrode, a second electrode, and at least one nanowire between the first electrode and the second electrode, with each nanowire connected at a first end to the first electrode and at a second end to the second electrode.

A method for operating an array of fluid sensors is provided. The method comprises:
providing an array of fluid sensors, each fluid sensor comprising
a first electrode,
a second electrode, and
at least one nanowire between the first electrode and the second electrode, with each nanowire connected at a first end to the first electrode and at a second end to the second electrode;
introducing at least one fluid to the fluid sensor; and
determining an aspect of the at least one fluid.

BRIEF DESCRIPTION OF THE DRAWINGS

FIGS. 1$a$-1$h$ are each a cross-sectional area, depicting an embodiment for the fabrication of a fluid sensor;

FIGS. 3$a$-3$c$ are each cross-sectional views that depict an embodiment of a nanowire and the development of a depletion region as a result of sensing an aspect of a fluid (depletion mode operation); and FIG. 4, on coordinates of dopant concentration (in $cm^{-3}$) and wire diameter (in nm), is a plot of the maximum dopant concentration as a function of wire diameter for complete depletion of a nanowire employed in an embodiment of a fluid sensor, such as depicted in FIG. 1$h$.

BEST MODES FOR CARRYING OUT THE INVENTION

Figure 2:
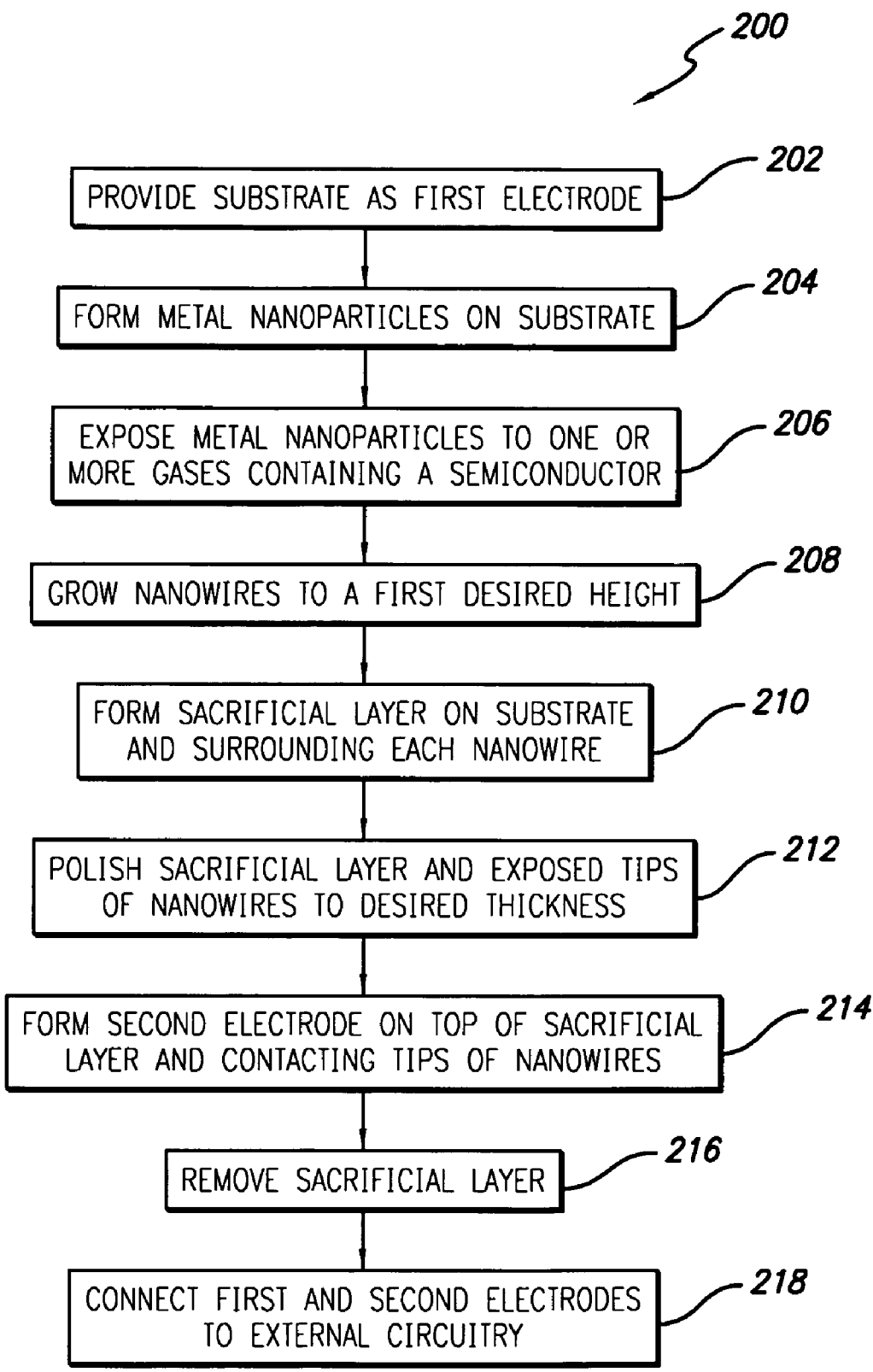
FIG. 2 is a flow chart, depicting an embodiment of the steps for fabricating the fluid sensor.

Reference is made now in detail to specific embodiments, which illustrates the best mode presently contemplated by the inventor for practicing the invention. Alternative embodiments are also briefly described as applicable.

In accordance with the teachings herein, a fluid sensing structure is fabricated using metal-catalyzed semiconductor nanowires as the sensing elements. The sensor contains at least one nanowire, and, in some embodiments, a plurality of nanowires, with contacts to the nanowires formed simultaneously using only coarse lithography. The nanowires are the sensing elements. As used herein, the fluid may be a gas or a liquid, as is well known.

Structure

As shown in FIGS. 1$a$-1$h$, the structure consists of a substrate 10, which subsequently becomes a first electrode upon completion of the sensor device 28 (shown in FIG. 1$h$). The substrate 10, which can be a silicon wafer, forms one contact, or electrode, of the sensing array.

In one embodiment, the substrate may be a silicon wafer. The wafer or regions of the wafer may be doped so that the resistance of the region between the nanowires and the remaining circuitry (or connections) is low compared to that of the nanowires. This remaining circuitry may be either on the same substrate as the sensor or on a separate substrate. Because of the large cross section of the substrate compared to the nanowires, even lightly doped silicon (about $10^{15}$ $cm^{-3}$) is conductive enough. In some embodiments, the doping may be in the range $10^{18}$ to $10^{20}$ $cm^{-3}$ to lower the resistance further. Either conductivity type (n or p) may be suitable and is determined by the elements to which it is connected (e.g., the input of an amplifier or other processing circuitry). If a connection is made through a metallic interconnection, the conductivity type is less important.

In other embodiments, the substrate 10 may comprise any material capable of supporting the nanoparticles 12 (although if the substrate is a catalytic material, separate nanoparticles might not be needed) and acting as an electrically conducting electrode; additional examples include, but are not limited to, germanium, alloys of silicon and germanium, gallium arsenide, and indium phosphide.

The substrate or first electrode 10 may also be isolated from the physical support (which could be a silicon wafer or something else, for example). The most likely case (other than a bulk silicon wafer) would be a silicon-on-insulator (SOI) wafer with a (111)-oriented top silicon layer electrically isolated over most of the area from the bulk substrate. The top silicon layer would be heavily doped (because of its limited cross sectional area), perhaps to $10^{18}$ to $10^{20}$ cm$^{-3}$. Electrical connections may then be made between the first electrode (SOI layer) and selected regions of the substrate, perhaps connecting to the input of an amplifier or other processing circuitry in the bulk substrate. In another embodiment, the substrate or first electrode 10 may also be a thin silicon (or other semiconductor) layer on an insulating substrate, such as sapphire.

The directional growth perpendicular to a (111) silicon surface may be employed, but other techniques to orient the nanowires could possibly be used to provide this directionality; for example, an electric field might cause the nanowires to grow perpendicular to the substrate surface (or at least have a substantial component of growth perpendicular to the substrate, as stated below). A wider range of substrates/first electrodes 10 is then possible, as long as it is conductive. The substrate/first electrode might comprise a catalyst so that the nanowires grow on it without adding catalyst nanoparticles, or it might not be a catalyst so that the catalyst nanoparticles can be placed on the substrate in the desired density or perhaps locations. A silicon layer of some sort is the most widely cited "substrate" for nanowire growth. Other semiconductors with adequate conductance may be suitable, and metals may also work as the substrate/first electrode 10. The metals or semiconductors forming the first electrode should be adequately stable at the nanowire growth temperature to remain electrically continuous after nanowire growth and other processing.

Metal nanoparticles 12 are formed on the substrate 10 (FIG. 1b). The formation of metal nanoparticles on semiconductor substrates is known, and is disclosed, for example, in application Ser. No. 10/281,678, filed Oct. 28, 2002, published as Publication No. 2004-0082178 on Apr. 29, 2004, and application Ser. No. 10/690,688, filed Oct. 21, 2003, published as Publication No. 2004-0079278 on Apr. 29, 2004, the contents of both of which are incorporated herein by reference. As used herein, a nanoparticle is a particle having all its dimensions measured in nanometers, typically less than 100 nm. The nanoparticles may be approximately spherical, having a diameter of less than about 100 nm, or may have other shapes, such as a cube or a flake.

Nanowires 14 are grown using the nanoparticles 12 as catalysts for wire growth (FIG. 1c). The nanowires 14 grow at an angle to the substrate plane, with nearly vertical growth being common and most conceptually easiest to visualize, but non-vertical orientation of the nanowires can be used if the vertical height of the nanowire is greater than the electrode separation.

A top, or second, electrode 20 is used to make the second contact to the nanowires 14, and current flows through the array of nanowires via leads 22, 24 (FIG. 1h). The number of mobile carriers in a nanowire 14 and thus its conductivity is modulated by a fluid 26 (or an aspect of the fluid) adsorbed on the surfaces of the nanowire or interacting with a functional coating (not shown) placed on the nanowire. Because of the large number of nanowires and the small volume of each, the surface to volume ratio is large. Modulation of the conductivity of the array is used to sense the presence and quantity of the fluid 26.

In some embodiments, a selective functional coating may be placed on the nanowire surface so that only certain species from the nearby gas or liquid can bind to the surface and modulate the conductance of the nanowire. For example, a DNA sensor may be functionalized with a particular probe DNA/PNA, which only binds the complementary DNA and does not significantly bind non-complementary DNA. An array of sensors with different sensitivity to different species may be used if the functional coating is not totally selective to a particular species.

Method of Fabrication

To fabricate the array, reference is made to both FIGS. 1a-1h and 2; FIG. 2 depicts an embodiment of a method 200 of fabricating the nanowire sensor. A substrate 10 is provided as a first, or bottom, electrode (FIG. 1a; step 202).

Metal nanoparticles 12 are formed on the substrate 10 (FIG. 1b; step 204). These nanoparticles 12 can be formed by evaporating a very thin layer (~atomic layer thickness) on the substrate 10 and annealing to condense the metal into individual particles 12, preferably with no metal on the substrate between the particles. Alternatively, the nanoparticles 12 can be deposited from a commercially available colloidal suspension of appropriately-sized nanoparticles. Or yet alternatively, the nanoparticles 12 can be deposited by chemical vapor deposition, which can be made selective to certain substrate materials so that they are only deposited on selected regions of the substrate (e.g., silicon, but not silicon oxide).

In general, the metallic nanoparticles 12 comprise a catalytic material capable of catalyzing the growth of nanowires 14. Accordingly, the nanoparticles 12 can include metals used to generate silicon nanowires, such as, but not limited to, titanium, gold, platinum, palladium, nickel, and manganese and their silicides. To generate germanium or silicon-germanium nanowires 14, the catalytic material can be, but is not limited to, gold. Nanowires of other semiconductor materials can also be grown by catalyzed growth. The catalyst for the growth of such semiconductor materials is, in many cases, known in the art.

After the nanoparticles 12 are formed, they are exposed to a gas or gases, shown at 16, containing a semiconductor (FIG. 1c; step 206). Deposition variables are adjusted so that the reaction rate of the gas 16 on the substrate 10 is small, while that on the metal particle 12 is much greater; the metal nanoparticle accelerates or catalyzes the decomposition of the gas. Atoms of the semiconductor material deposited on the nanoparticle 12 diffuse through or around the nanoparticle, which may be either in the liquid or solid state during wire formation, and precipitate on the underlying substrate 10, pushing the metal nanoparticle up and leaving a columnar semiconductor deposit 14 (i.e., a nanowire) behind. The diameter of the nanowire 14 is similar to that of the nanoparticle 12. In some embodiments, a single nanoparticle 12 is formed on the substrate 10, generating a single nanowire 14.

In an embodiment, the substrate 10 comprises silicon and the metal nanoparticles 12 comprise gold. In this example, it is desired to grow germanium (Ge) nanowires 14. This is done by introducing a gaseous source 16 containing Ge, such as germane (GeH$_4$). The germane molecules react with the gold nanoparticles 12, forming Ge atoms by catalyzed surface reaction and releasing H$_2$; the Ge atoms diffuse through or around the gold nanoparticles 12 to the substrate or already formed regions of the nanowire, where they precipitate, thereby forming the nanowires 14. Alternatively, the Ge atoms can be provided by physical deposition techniques, such as laser ablation, followed by adsorption and surface diffusion.

In another embodiment, the substrate 10 comprises silicon and the metal nanoparticles 12 comprise any of the metals previously listed above, such as gold. In this case, the gaseous source 16 contains Si, such as silane (SiH$_4$) or dichlorosilane, and silicon nanowires 14 are formed, using a process essentially similar to that outlined in the previous paragraph.

The nanowires 14 are grown until their vertical height is greater than the desired separation of the electrodes 10, 20 (step 208). This separation determines one dimension of the sensing region. The grown connection between the substrate 10 and the grown nanowire 14 forms the bottom electrical contact to the nanowire. The resulting structure is shown in FIG. 1c.

A temporary, "sacrificial" layer 18 of easily-etched material ("etchable material") is then formed on the substrate 10 and surrounding each nanowire 14, as depicted in FIG. 1d (step 210). The thickness of this sacrificial layer 18 (on a bare substrate 10) is equal to or greater than the desired electrode separation. It is likely to be thicker in the region immediately adjacent each nanowire 14. The structure is then polished to smooth the top of the structure and to reduce the thickness of the sacrificial layer 18 to a thickness slightly greater than the desired electrode separation, thereby also removing the metal nanoparticles 12 (step 212).

By "easily-etched" is meant that the sacrificial layer 18 is etched at a rate faster than the etch rate of the nanowires 18. For example, for nanowires 14 comprising silicon, a suitable material for the sacrificial layer 18 would be silicon dioxide, which is easily etched with hydrofluoric-acid containing solutions. The etching rate of high-quality, undoped silicon dioxide can be controlled by adjusting the composition of the HF in the etching solution. For a mixture of 10 parts wafer to 1 part concentrated (49%) HF, the etch rate is approximately 30 nm/min, while the etching rate of silicon is negligible (<<1 nm/min). The etch rate of lower-density silicon dioxide can be 2 to 6 times as great. The etch rate of the silicon dioxide layer can be increased substantially by adding materials, such as phosphorus or boron. Such phosphorus-doped silicon dioxide (PSG) containing 10% phosphorus can be etched at least 4 to 20 times as rapidly in a given concentration of HF as undoped silicon dioxide. Alternatively, organic layers, such as polymer layers, might be used because only low temperature processing steps are used after the sacrificial layer is formed. A polymer layer might be more difficult to polish, but doable (e.g., it is used successfully in integrated-circuit processing), but it can be removed in an organic solvent that would not attack the nanowires.

The sacrificial layer 18 can then be thinned slightly so that the tops of the nanowires protrude slightly above the top of the sacrificial layer to provide more contact area between the top electrode and the nanowires, as shown in FIG. 1e. Additional dopant can be added to the tops of the nanowires 14, if desired, to reduce the contact resistance of the subsequently formed nanowire/top electrode contact. The separation distance between the two electrodes 10 and 20 can be less for a gas sensor than for a liquid sensor. For a gas sensor, 0.5 to 20 micrometers may be typical. For a liquid sensor, 5 to 20 micrometers may be typical. The ability to form sacrificial layer 18 and the ability to grow long nanowires limits the upper practical separation. The lower limit is set by the ability of the gas or liquid to flow readily into the space between electrodes.

The electrode metal 20 is then deposited and patterned with a large dimension consistent with coarse lithography or other patterning technique (FIG. 1f; step 214). This electrode 20 physically and electrically contacts many nanowires 14 and is very much larger in lateral dimension that the nanowire diameter. Thus, patterning the large top electrode 20 does not require fine lithography. In some embodiments, the top electrode 20 comprises a metal deposited by physical vapor deposition. This method of deposition limits the temperature so that a polymer sacrificial layer (if a polymer is used) is not degraded. Examples of such metals include, but are not limited to, gold, tungsten, titanium, platinum, aluminum, and copper. The top electrode 20 may alternatively comprise a semiconductor, such as polycrystalline silicon.

After the top electrode 20 is defined, the sacrificial layer 18 is etched laterally until it is removed between the two electrodes 10, 20 in the sensing area, forming the sensing cavity (FIG. 1g; step 216). The structure 28 can be annealed at a moderate temperature to reduce the contact resistance between the nanowires 14 and the top contact 20. The surfaces of the nanowires can be passivated (if not done earlier) or functionalized to make them more selective.

The structure 28 can then be appropriately packaged so that the sensing cavity is exposed to the fluid 26 being sensed (FIG. 1h). Species from the fluid 26 on or near the surfaces of the nanowires modulate the conductivity of the nanowire(s) 14, either by changing the physical size of the conducting region (depletion mode) or by inducing mobile carriers near the surfaces of the nanowires (accumulation or inversion mode). Specifically, the region of the nanowire that has mobile charge carriers is the conducting region. In depletion-mode operation, carriers are pushed away from the regions near the surfaces so only the inner core is conducting. A charge provided by the material being sensed attracts or repels carriers, changing the thickness of the depleted region, so the diameter of the conducting core changes. In accumulation or inversion modes of operation, mobile charge is induced by the material being sensed, and this additional mobile charge is located near the surface of the nanowire. The conducting region that is modulated is then near the surface. Accumulation mode will have parallel conductance in the regions away from the surface, but these will not be substantially affected by the material being sensed.

The bottom and top electrodes 10, 20 are connected to external signal processing circuitry via leads 22, 24, respectively (step 218), which may include on-chip circuitry or off-chip circuitry. At least a portion of the signal processing circuitry can be fabricated in the underlying substrate (if it is a semiconductor, such as silicon) before the array of nanowires 14 is formed. Placing some of the circuitry physically close to the sensing array is advantageous in improving the signal to noise ratio; the signal can be amplified before noise is added when the signal is transmitted over a long distance and between different physical units.

Electrode 10 may be anywhere from 10 nm thick to the entire thickness of the substrate (0.5 to 1 mm for a silicon wafer), although the lower limit is governed by resistance that increases as the electrode thickness is reduced. Electrode 20 may be anywhere from 10 nm to a few micrometers thick, limited by the ability to conveniently deposit and define the top electrode.

Additional Features

The diameter of the nanowire 14 can be adjusted to provide the desired surface to volume ratio for optimum detection by controlling the diameter of the metal nanoparticles 12, although precise uniformity of the diameters of different nanowires is not required. Typical diameters are 5 to 200 nm; when operating in depletion mode, the sensitivity is greater if the conducting core is small; this depends on the doping, so there is a relationship between the doping and the diameter for the nanowires. For complete depletion, the relation between the nanowire radius and the doping is given by the following formula; for depletion-mode operation, the nanowire may not be completely depleted, but this formula for the maximum depleted radius $r_{d\,max}$ gives an idea of the tradeoffs.

$$r_{d\max} = \sqrt{\frac{12\varepsilon_s \phi_B}{qN_D}} \approx \frac{D}{2}$$

$$N_{D\max} \approx 2 \times 10^8 / D^2$$

where $\varepsilon_s$ is the permittivity of the semiconductor comprising the nanowire, $\phi_B$ is the bulk potential corresponding to the dopant concentration in the semiconductor nanowire, q is the magnitude of the charge of one electron, $N_D$ is the dopant concentration in the semiconductor nanowire (in cm$^{-3}$), and D is the nanowire diameter (in cm).

FIG. 3a depicts a portion of the nanowire 14. FIG. 3b depicts the fluid 26 on a portion of the nanowire 14 and the formation of a depletion region 30 associated with the fluid. FIG. 3c depicts complete depletion of the nanowire 14 in the region of the fluid 26.

Dopant atoms can be added to the nanowires 14 during their growth by introducing a gas containing the desired dopant atoms, or the nanowires can be doped after deposition, most readily from a gaseous source containing the dopant atoms or by diffusion from a doped oxide, possibly using doping included in the sacrificial layer.

The large number of nanowires 14 provides structural support for the top electrode, as well as acting as the sensors. In some embodiments, the number of nanowires needed for structural support may be at least about 4/$\mu m^2$ for 100 nm diameter nanowires; if the wires are thin, more may be needed or, alternatively, additional structural support (mechanical rigidity) may be provided as follows: a portion of the sacrificial layer 18, may be retained to provide the mechanical support, or regions of another material (not shown) may be inserted to provide additional mechanical support. The additional supporting region can be formed on the substrate before wire growth and patterned using only coarse lithography. This supporting region can also act as a polish stop during polishing of the nanowires 14 and sacrificial layer 18, thus enhancing control of the fabrication process. With a supporting region, only one nanowire 14 may be employed.

The semiconductor material comprising the nanowires 14 typically is silicon or germanium to allow well-developed processing techniques to be used; however, other semiconductors can be used to take advantage of their specific characteristics. Examples of such other semiconductors include, but are not limited to, $Si_{1-x}Ge_x$ (where 0<x<1), GaAs, and InP.

The nanowires 14 may be provided with a functional coating that is specific to sensing specific gases. For example, a nanowire DNA sensor for liquids has been described by Z. Li et al in "Sequence-specific label-free DNA sensors based on silicon nanowires," Nano Letters, Vol. 4, pp. 245-247 (2004). Examples of functional coatings are well known in the art.

An array of fluid sensors may be provided, and at least one fluid may be introduced onto the fluid sensors in the array. An aspect of the fluid(s) may then be determined. For example, the fluid sensor may be used to determine the presence of a class of compounds, such as hydrocarbons, or the quantity of the species in the fluid or the identity of a species, such as a specific hydrocarbon.

In an embodiment, each fluid sensor may be provided with a functional coating having a different response to different species. A signal from each fluid sensor in the array may be determined upon exposure to the fluid to form a set of signals and the set of signals may be processed to determine the identity or quantity of each species in the fluid being analyzed.

What is claimed is:

1. A method of fabricating a fluid sensor, said method comprising:
   providing a substrate comprising a first electrode;
   forming at least one metal nanoparticle on said substrate;
   exposing said at least one metal nanoparticle to at least one gas containing a semiconductor for a period of time sufficient to grow a corresponding at least one nanowire of a first predetermined length;
   forming a layer of an etchable material on the substrate and surrounding said at least one nanowire;
   optionally thinning said layer of said etchable material to expose a top of said at least one nanowire, thereby providing said at least one nanowire with a second predetermined length that is less than said first predetermined length;
   depositing a layer of a metal on top of said layer of etchable material and patterning said layer of metal to form a second electrode;
   at least partially removing said layer of said etchable material, sufficient to expose at least one said nanowire.

2. The method of claim 1 wherein said first electrode comprises an electrically conductive material.

3. The method of claim 2 wherein said electrically conductive material is selected from the group consisting of silicon, tungsten, and gold.

4. The method of claim 1 wherein said at least one nanoparticle is selected from the group consisting of titanium, gold, platinum, palladium, nickel and manganese and silicides thereof.

5. The method of claim 1 wherein said at least one gas is selected from the group consisting of silane, germane, and dichlorosilane.

6. The method of claim 1 wherein said first predetermined length is greater than a specified distance separating said first electrode and said second electrode.

7. The method of claim 1 wherein said at least one nanowire comprises a material selected from the group consisting of silicon, germanium, $Si_{1-x}GaAs$, and InP.

8. The method of claim 1 wherein said layer of etchable material is selected from the group consisting of silicon dioxide, phosphorus-doped or boron-doped silicon dioxide, and organic materials.

9. The method of claim 1 wherein said layer of etchable material is thinned by mechanical polishing or chemical mechanical polishing, sufficient to remove any nanoparticles remaining on top of said nanowires.

10. The method of claim 1 wherein said second predetermined length is substantially equivalent to a specified distance separating said first electrode and said second electrode.

11. The method of claim 1 wherein said second electrode comprises at least one metal selected from the group consisting of gold, tungsten, titanium, platinum, aluminum, and copper.

12. The method of claim 1 wherein said layer of etchable material is at least partially removed by wet chemical etching or isotropic plasma etching.

13. The method of claim 1 wherein said layer of etchable material is completely removed, leaving a plurality of said nanowires to support said second electrode over said first electrode.

14. The method of claim 1 further including electrically connecting said first electrode and said second electrode to external signal processing circuitry.

15. The method of claim 1 further including providing said at least one nanowire with a functional coating that is specific to sensing specific species in a fluid.

16. A method of fabricating an array of fluid sensors, each fluid sensor sensitive to a specific species in a fluid being analyzed, each fluid sensor formed by the following steps:

providing a substrate comprising a first electrode;

forming at least one metal nanoparticle on said substrate;

exposing said at least one metal nanoparticle to at least one gas containing a semiconductor for a period of time sufficient to grow a corresponding at least one nanowire of a first predetermined length;

forming a layer of an etchable material on the substrate and surrounding said at least one nanowire;

optionally thinning said layer of said etchable material to expose a top of said at least one nanowire, thereby providing said at least one nanowire with a second predetermined length that is less than said first predetermined length;

depositing a layer of a metal on top of said layer of etchable material and patterning said layer of metal to form a second electrode;

at least partially removing said layer of said etchable material, sufficient to expose at least one said nanowire, said method further comprising;

providing said at least one nanowire of each said fluid sensor with a functional coating that is specific to sensing a specific species in said fluid, each fluid sensor thereby sensing a different species.

* * * * *

UNITED STATES PATENT AND TRADEMARK OFFICE
CERTIFICATE OF CORRECTION

PATENT NO. : 7,235,475 B2
APPLICATION NO. : 11/022123
DATED : June 26, 2007
INVENTOR(S) : Theodore I. Kamins It is certified that error appears in the above-identified patent and that said Letters Patent is hereby corrected as shown below:

In column 4, line 29, after "substrate" insert -- 10 --.

In column 8, line 55, in Claim 5, delete "dichiorosilane" and insert -- dichlorosilane --, therefor.

In column 8, line 61, in Claim 7, delete "$Si_{1-x}$" and insert -- $Si_{1-x}Ge_x$, --, therefor.

Signed and Sealed this

Sixth Day of October, 2009

David J. Kappos
*Director of the United States Patent and Trademark Office*